(12) United States Patent
Messina

(10) Patent No.: US 9,561,360 B1
(45) Date of Patent: Feb. 7, 2017

(54) WRITING UTENSIL WITH ACTIVE NERVE STIMULATION

(71) Applicant: Raymond M. Messina, Windham, NH (US)

(72) Inventor: Raymond M. Messina, Windham, NH (US)

(*) Notice: Subject to any disclaimer, the term of this patent is extended or adjusted under 35 U.S.C. 154(b) by 258 days.

(21) Appl. No.: 13/908,692

(22) Filed: Jun. 3, 2013

Related U.S. Application Data

(60) Provisional application No. 61/654,681, filed on Jun. 1, 2012.

(51) Int. Cl.
*A61N 1/05* (2006.01)
*A61N 1/04* (2006.01)
A61N 1/375 (2006.01)
A61N 5/06 (2006.01)

(52) U.S. Cl.
CPC ........... *A61N 1/0472* (2013.01); *A61N 1/0456* (2013.01); *A61N 1/375* (2013.01); *A61N 2005/0644* (2013.01)

(58) Field of Classification Search
CPC .................... A61N 2005/0644; A61N 1/0456; A61N 1/375; A61N 1/0472
USPC .................................................. 607/145, 146
See application file for complete search history.

(56) References Cited

U.S. PATENT DOCUMENTS

| 4,981,146 A | 1/1991 | Bertolucci | |
| 5,244,299 A * | 9/1993 | Chu | A61H 23/0263 401/195 |
| 6,228,103 B1 * | 5/2001 | Grey | A61H 39/04 601/107 |
| 6,582,449 B2 | 6/2003 | Grey et al. | |
| 2001/0023359 A1 * | 9/2001 | Grey | A61H 39/04 606/204 |
| 2004/0127939 A1 * | 7/2004 | Grey | A61N 1/36014 606/204 |
| 2006/0147246 A1 * | 7/2006 | Richards | B43K 23/008 401/6 |
| 2009/0236153 A1 * | 9/2009 | Kyung | G06F 1/20 178/19.01 |

* cited by examiner

Primary Examiner — Michael Kahelin
Assistant Examiner — Minh Duc Pham
(74) Attorney, Agent, or Firm — Thomas P. O'Connell; O'Connell Law Firm

(57) ABSTRACT

A writing utensil for providing active nerve stimulation to the fingertips of a user. The writing utensil has a body portion, a tip portion with a marking tip, and an active stimulator with active stimulation surfaces retained adjacent to the distal end of the body portion to be engaged by the fingertips of the user. The active stimulator has an active state where active stimulation is provided to the fingertips of the user and an inactive state where active stimulation is not provided. The active stimulator can comprise mechanical movement mechanisms where nodules, such as rotatable cam nodules with eccentric portions, periodically extend in relation to the active stimulation surfaces. Additionally or alternatively, the active stimulator can comprise electrical pulse mechanisms for imparting electrical impulses to fingers disposed in contact therewith. Active nerve stimulation can be provided simultaneously, in series, or in some other pattern.

12 Claims, 6 Drawing Sheets

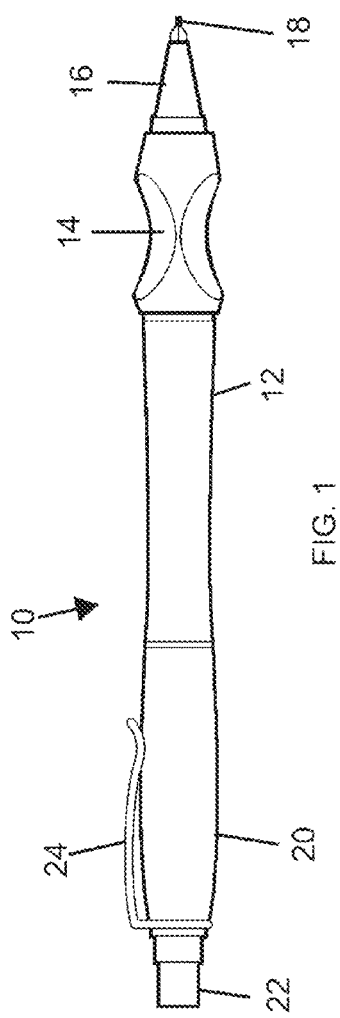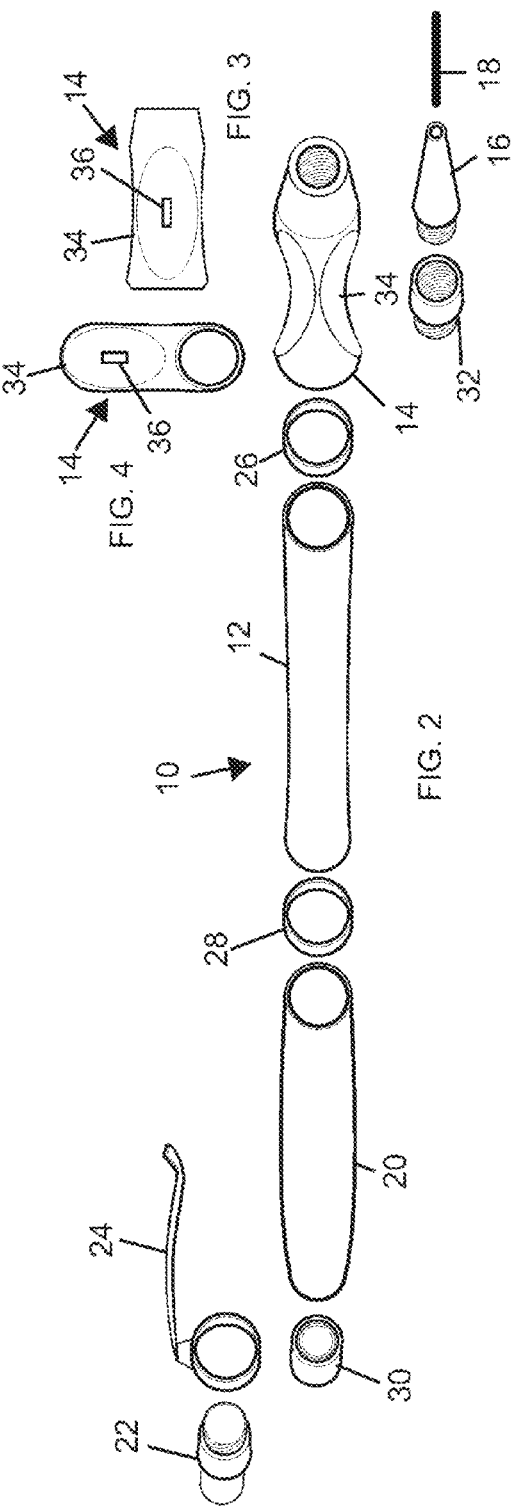

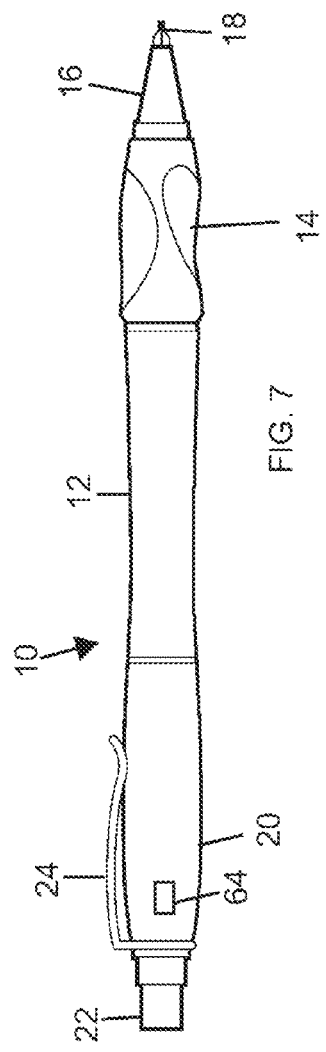
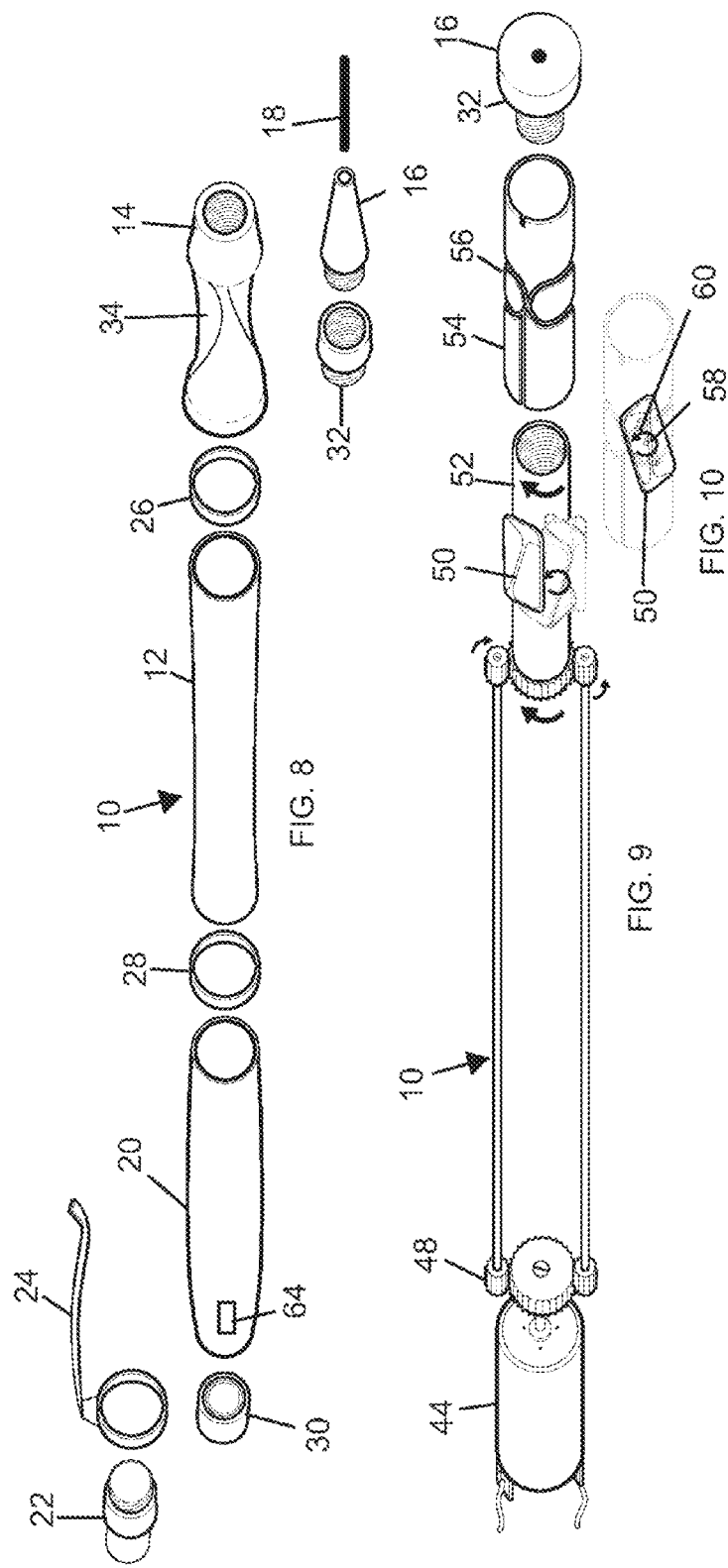

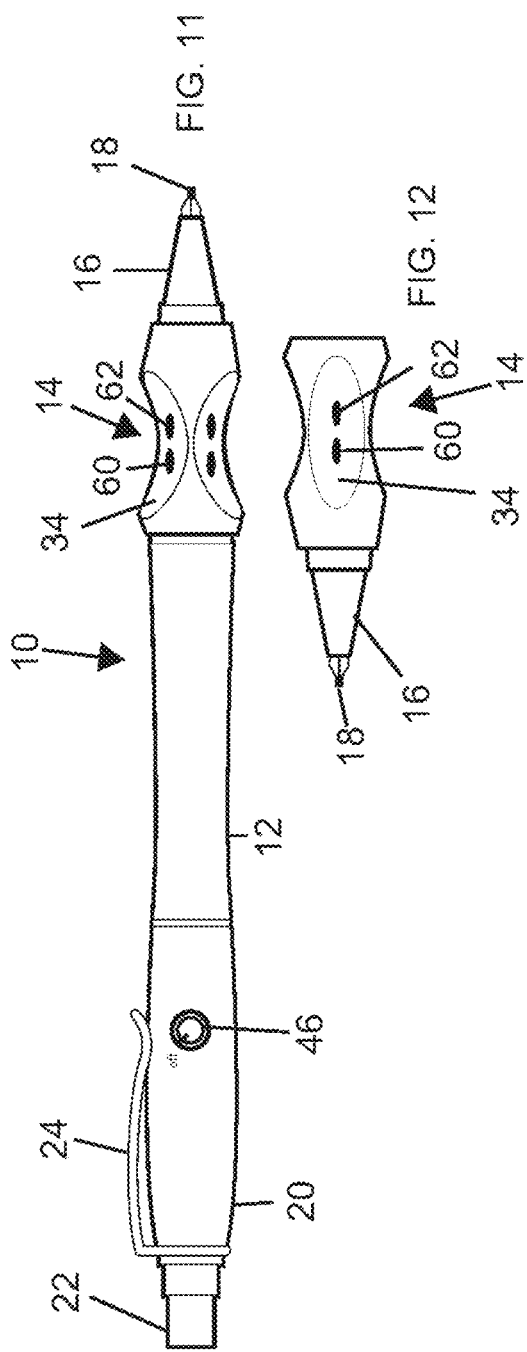

WRITING UTENSIL WITH ACTIVE NERVE STIMULATION

FIELD OF THE INVENTION

The present invention relates generally to writing utensils and the stimulation of human nerves. More particularly, disclosed and protected herein is a writing utensil with means for actively stimulating the nerves in human fingers.

BACKGROUND OF THE INVENTION

Repetitive manipulation of the thumb and fingers in the handwriting process helps prime and activate the left brain. The left brain manages executive functions, such as planning, monitoring, organizing, revising and attending—skills critical to educational achievement and self management. All forms of writing increase left brain dominance over the right. Being the most abstract, the alphabet enhances the left brain values most.

As an intentional movement, handwriting's impulses are the essence of the emotional life force. Handwriting has been characterized as "brainwriting," akin to a legible EEG. Writing by hand is the most basic of the 3'Rs, and it is the unrecognized foundation for developing the other 2Rs. The ability to regulate one's handwriting reveals that a person has learned to harness his or her emotional energy flow and that impulse control has been achieved. As the process integrates the specialized powers of the brain hemispheres, it enables a person to direct emotional energy so that being functionally productive or goal directed is possible.

The median nerve runs through the carpal tunnel of the wrist and, apart from the little finger, connects with the thumb and all fingers of the hand. As such, the median nerve serves as a peripheral gateway to the central nervous system. This is reflected in the fact that the sensory distribution of the hand has a large cortical representation in the brain. Median nerve stimulation has been found to activate the entire central nervous system.

It is believed that this peripheral stimulus is responsible for releasing hormones and neurotransmitters. Hormones and neurotransmitters that could be released include Norepinephrine, Acetylcholine, and Dopamine. Norepinephrine has been found to contribute to alertness and arousal, and reward, to play a large role in attention and focus, and to increase the alteration detection rate. Acetylcholine enhances sensory perceptions and attentiveness while slowing the heart rate when functioning. It can play a role in decision-making, and it can relax and calm while exciting and arousing through a sense of reward. In this regard, it will be noted that chronic stress causes a chemical change that shuts down learning and undermines the brain's ability to lock information into memory. Finally, Dopamine has been determined to be responsible for reward-driven learning.

Humans are born with a natural flow of energy, but stress and other emotions clog and disrupt the flow. Accordingly, the present inventor has appreciated that preventing such clogging and disruption, particularly during the crucial stages of early learning and brain development, would be highly advantageous.

It will again be noted that handwriting and the static nerve stimulation derived therefrom tend to benefit the brain. However, the present inventor has theorized that simultaneous pressure on all three median nerves of the gripping fingers restricts flow and brain development and usage. This incorrect, static pressure causes what can be referred to as muscular armoring. Humans adapt to muscular armoring while learning to write, and it stays with us.

In this regard, one will note the six meridians in the human hand. Each finger plays a key role, and their character needs have to be considered:

Thumb (Lung Meridian: Metal-energy yin (−) organ;
Pointer Finger (Large Intestine: Metal-energy yang (+) organ;
Middle Finger (Pericardium: Fire-energy yin (−) organ;
Ring Finger (Triple Burner: Fire-energy yang (+) organ;
Little Finger (Heart Meridian: Fire-energy yin (−) organ; and
Little Finger (Small intestine: Fire-energy yang (+) organ.

Considering these six meridians in the hand and their characteristics, including psycho-emotional aspects, it can be argued reasonably that those meridians control our emotions. Many seek through sundry methods and for various purposes to achieve a pure state of mind, referred to as Mushin or "without mind" in Japanese. For example, very highly trained martial artists are said to enter the Mushin mental state during combat. The ability to facilitate mental purity and brain development and function, particularly in the young, would be highly advantageous.

The inventor has further recognized that the history of human brain development has had three distinct phases: the reptilian brain, the limbic or mammal brain, and the neocortical or human brain. It would represent a marked advance to all humankind if an invention were disclosed that could take the brain, even if not structurally but functionally, to another phase. If that is achieved, it will further be shown that we are not enjoying the full function and benefit of our bodies as they were intended and designed. The use of the hand and energy flowing at will in and out of the hand will not only bring our minds to a different level but would also bring us as creatures to a different level. The brain, the body, and the Universe can be calm, relaxed, focused, and emotionally balanced.

With this admittedly ambitious path laid out, it will be recognized as further foundation that the human body is composed of cell masses that are logically organized into various tissue in four general classes: muscle, nerve, epithelial, and connective tissue. In turn, the various tissue types are organized into organs, which operate as systems. Each system, such as the circulatory, respiratory, digestive, urinary, musculoskeletal, immune, nervous, endocrine, reproductive, and intebumentary systems, has a clearly defined function.

The nervous system, for example, regulates and coordinates many activities in the body. It detects changes in the internal and external environments and relates to states of consciousness, learning, and cognition. In addition to its physiological function, namely the transmission of nerve impulses, the nervous system serves to distribute energy to the body tissues and organs. The nervous system is also an energetic system. However, the tips of our fingers can be considered to have the least amount of this energy flow, particularly in view of muscular armoring.

Living organisms emit vibrations at a frequency of 300 to 2,000 nanometers. This energy is called biofield or bioplasma. This energy is stronger when people are more successful at transferring or projecting the bioenergy. Muscular armoring is an intrinsic part of neurotic adaptation with reduced vitality, reduced sensation & feeling, and a reduction in the flow of emotion and other important functions. Release of this muscular armoring brings about pulsatory movement and a streaming sensation, which subjectively are experienced as a flow of energy and objectively are concomitant with such things as increased emotional release, warmth, vitality, and liveliness of tissue. When our nervous system tissue is readily available to energy flow, we experience ourselves as more connected to and able to truly occupy our physical being. It would be advantageous, therefore, to create a palpable sense of flow, connection, awareness, and warmth and to intensify the frequency of the electromagnetic fields from our hands. Similarly advantageous would be to create a more open flow, one that flows intensely and naturally by clearing and opening the nerves for better energy flow.

SUMMARY OF THE INVENTION

With a knowledge of the foregoing, the present inventor set forth with a number of objects with the most basic being to provide a utensil that promotes the flow of energy, hormones, and neurotransmitters in the human body through active stimulation of nerves in the human hand.

A related object of the invention is to provide a utensil that tends to prevent the clogging and disruption of the flow of such hormones and neurotransmitters, particularly during the crucial stages of early learning and brain development.

A further object of embodiments of the invention is to provide a utensil with active nerve stimulation that amplifies such flow and renders it more natural.

A resultant object of the invention is to provide a utensil with nerve stimulation that can operate to make users more focused, calm and mentally, emotionally and physically balanced.

Still another object of embodiments of the invention is to provide a utensil that actively stimulates the median nerve and the hand in general with consideration to the six meridians in the hand and their relation to each other and the rest of the parts of the body.

A broader object of the invention is to provide a utensil with nerve stimulation that is capable of taking the brain to a further phase of development and, in so doing, to permit users to realize the full function and benefit of our bodies as they were intended and designed.

Yet another object of the invention is to provide a utensil that can create a palpable sense of flow, connection, awareness, and warmth and that tends to intensify the frequency of the electromagnetic fields from our hands.

In carrying forth the aforementioned objects, an embodiment of the writing utensil with active nerve stimulation disclosed herein provides active stimulation to the fingertips of a user by use of a body portion with a proximal end and a distal end, a tip portion coupled to the distal end of the body portion wherein the tip portion has means for retaining a marking tip, and an active stimulator. The active stimulator has at least one active stimulation surface disposed adjacent to the distal end of the body portion to be engaged by the tips of the fingers of the user. The active stimulator has an active state where active stimulation is provided to the fingertips of the user in contact with the active stimulation surface and an inactive state where active stimulation is not provided to the fingertips of the user in contact with the active stimulation surface.

In certain practices of the invention, the writing utensil can have first, second, and third active stimulation surfaces, each stimulation surface for engaging a fingertip of the user. Each active stimulation surface can have a concave curvature or an anticlastic curvature for receiving and engaging the fingertips of the user.

Under certain embodiments, the active stimulator has at least one mechanical movement mechanism with an inactive state and an active state where cyclical mechanical movement is exhibited in relation to the active stimulation surface. Where first, second, and third active stimulation surfaces are provided, each stimulation surface can engage a fingertip of the user and the mechanical movement mechanism can produces a periodic, potentially in a sequential or other pattern, extension relative to the active stimulation surfaces when the active stimulator is in an active state. By way of example, the mechanical movement mechanism can have at least one nodule and means for cyclically causing at least a portion of the nodule to extend periodically relative to the active stimulation surface. The nodule can be a cam nodule with an eccentric portion, and the means for cyclically causing at least a portion of the nodule to extend periodically relative to the active stimulation surface can be a means for rotating the cam nodule. In such embodiments, the active stimulator can further comprise a motor and a power source for the motor. Still further, a resilient sheet can overlie the can nodules for being interposed between the fingertips of the user and the cam nodules.

In other embodiments, the mechanical movement mechanism can comprise a motor, a power source for the motor, an inner sleeve, a stimulation member with at least one follower wherein the stimulation member is retained to rotate relative to the inner sleeve, a guide sleeve concentrically disposed with the inner sleeve, and guide channels in the guide sleeve for receiving the follower of the stimulation member. Under such constructions, rotation of the inner sleeve will cause the stimulation member to travel circumferentially in relation to the guide sleeve and the writing utensil.

In alternative manifestations of the invention, the active stimulator can comprise an electrical pulse system with an active state where electrical impulses are imparted to a finger disposed in contact with the active stimulation surface and an inactive state where electrical impulses are not imparted to a finger disposed in contact the active stimulation surface. Again, the active stimulator can have first, second, and third active stimulation surfaces. Each stimulation surface can engage a fingertip of the user, and the electrical pulse system, when in an active state, imparts electrical impulses to fingers disposed in contact with the active stimulation surfaces. The electrical pulse system can include negative and positive electrodes spaced on the active stimulation surface for passing electricity from the writing utensil to a finger of the user in contact with the positive and negative electrodes. A control mechanism, such as a switch, dial, or other control means, can be employed for actuating the active stimulator between active and inactive states and for adjusting other operational parameters.

One will appreciate that the foregoing broadly outlines certain goals and embodiments of the invention to enable a better understanding of the detailed description that follows and to instill a better appreciation of the inventor's contribution to the art. These and in all likelihood further objects and advantages of the present invention will become obvious not only to one who reviews the present specification and drawings but also to those who have an opportunity to make use of an embodiment of the handwriting utensil disclosed herein. However, it will be appreciated that, although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

BRIEF DESCRIPTION OF THE DRAWINGS

In the accompanying drawing figures:

FIG. 1 is a view in side elevation of a writing utensil with active nerve stimulation pursuant to the invention;

FIG. 2 is an exploded perspective view of the writing utensil with active nerve stimulation of FIG. 1;

FIG. 3 is a view in side elevation of the active nerve stimulation portion of the writing utensil of FIG. 1;

FIG. 4 is a perspective view of the active nerve stimulation portion of the writing utensil of FIG. 1;

FIG. 7 is a view in side elevation of an alternative writing utensil with active nerve stimulation pursuant to the invention;

FIG. 8 is a partially exploded perspective view of the writing utensil with active nerve stimulation of FIG. 7;

FIG. 9 is an exploded perspective view of the motorization and stimulation portions of the writing utensil with active nerve stimulation of FIG. 7;

FIG. 10 is a perspective view of a stimulation portion of the writing utensil with active nerve stimulation of FIG. 7;

FIG. 11 is a view in side elevation of a further embodiment of the writing utensil with active nerve stimulation disclosed herein;

FIG. 12 is a view in side elevation of the stimulation and tip portions of the writing utensil with active nerve stimulation of FIG. 11.

DETAILED DESCRIPTION OF PREFERRED EMBODIMENTS

Figure 5:
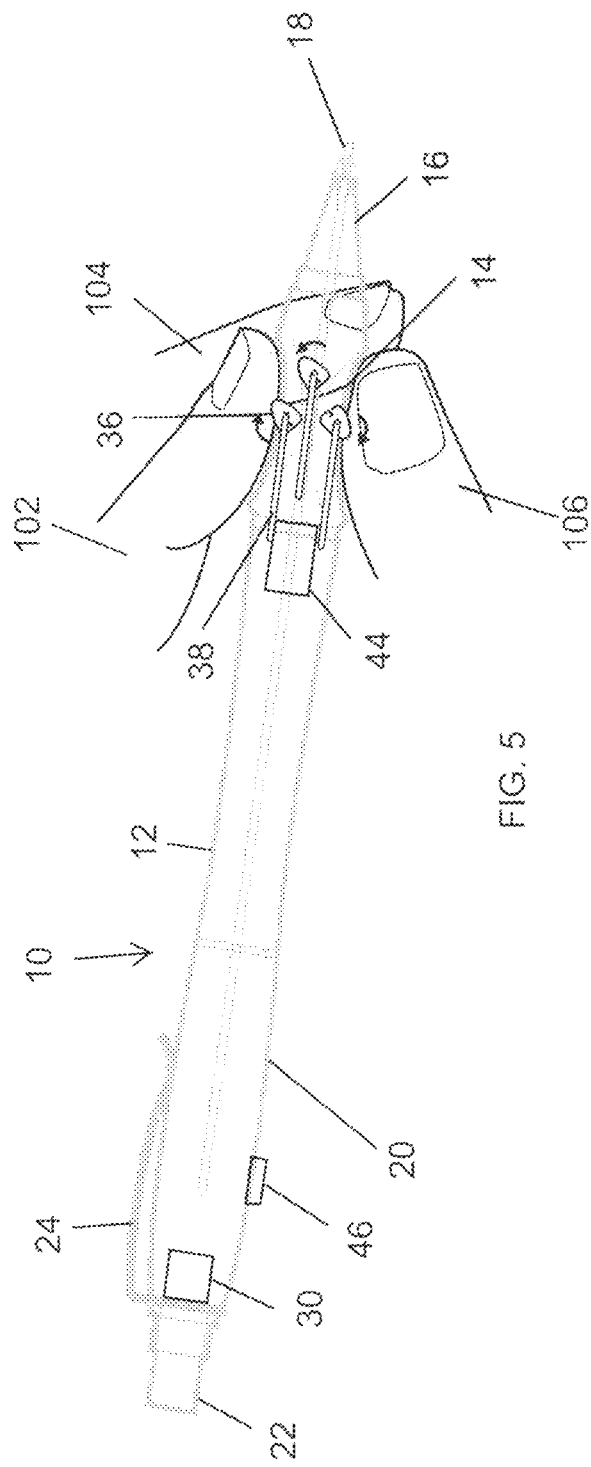
FIG. 5 is a partially sectioned perspective view the writing utensil with active nerve stimulation being gripped by a human hand.

It will be appreciated that the writing utensil disclosed herein is subject to varied embodiments. However, to ensure that one skilled in the art will be able to understand and, in appropriate cases, practice the present invention, certain preferred embodiments of the broader invention revealed herein are described below and shown in the accompanying drawing figures.

Before any particular embodiment of the invention is explained in detail, it must be made clear that the following details and illustrations of inventive concepts are mere examples of the many possible manifestations of the invention. It will be further appreciated that, while the present discussion of the invention may relate to certain types of writing implements to provide examples of possible exploitations of the invention, the writing utensil disclosed herein is not so limited and may be readily applied to other writing utensils and potentially other utensils except as it might be expressly limited.

In carrying forth the foregoing objects, an embodiment of a writing utensil with active nerve stimulation pursuant to the present invention is indicated generally at 10 in FIGS. 1 and 2. There, the writing utensil 10 has a body portion formed by a central tubular body member 12, a proximal tubular body member 20, and a distally disposed active nerve stimulation portion 14. Each of the tubular members 12 and 20 may pursue a contoured configuration, and no limitation as to the shape or construction of the members 12 and 20 should be interpreted or applied by the use of the term tubular.

The central tubular body member 12 is coupled to the proximal tubular body member 20 with an O-ring 28 interposed therebetween, and the central tubular body member 12 is coupled to the active nerve stimulation portion 14 with an O-ring 26 interposed therebetween. The tubular body members 12 and 20, the O-rings 26 and 28, and the active nerve stimulating portion 14 can be coupled in any effective way, such as by threaded engagement, by snap-fit engagement, by adhesive, by sonic welding, by unitary formation, or any other method or combination thereof.

A replaceable eraser 22 is retained at the proximal end of the tubular body member 20 with a pocket clip 24 retained by having a ring portion thereof interposed between the replaceable eraser 22 and the tubular body member 20. A conical tip portion 16, which could be magnetized to provide further physiological benefit and impact, is retained at the distal end of the active nerve stimulating portion 14 by a mutual threaded engagement between a coupling member 32 and the nerve stimulating portion 14 to the proximal end thereof and the tip portion 16 to the distal end thereof. Finally, a marking tip, which in this embodiment comprises a pencil lead 18, can be retained to extend and retract relative to the tip portion 16 and the writing utensil 10 in general.

While the present embodiment is depicted as a mechanical pencil, it will again be noted that the type of writing utensil 10 is of little consequence. The writing utensil 10 could readily comprise an ink pen, a marker, a paint brush, or any other type of writing or other handheld utensil 10. The pencil lead 18, the ink cartridge, or any of the other aspects of the writing utensil 10 can otherwise be standard.

By combined reference to FIGS. 1 through 5, the active stimulation portion 14 is disposed to be engaged by the tips of the user's pointer finger 102, middle finger 104, and thumb 106 in a proper utensil grip. To facilitate and promote proper gripping, the active stimulation portion 14 in this embodiment has first, second, and third evenly spaced stimulation surfaces 34, but the invention need not be so limited. Each stimulation surface 34 presents an ergonomic surface with a concave or anticlastic curvature for affirmatively receiving and engaging the user's fingers 102, 104, and 106. As such, the portion of the active stimulation portion 14 local to the stimulation surfaces 34 pursues an approximately triangular cross-section.

The active stimulation portion 14 has means for producing an active stimulation of the tips of one or more of the fingers 102, 104, and 106 of the user. The means for producing active stimulation could vary widely within the scope of the invention. For example, as described below, embodiments of the invention are contemplated where electrical pulses, potentially high voltage but safe electrical pulses, could be emitted from one, two, or each of the stimulation surfaces 34 or the stimulation portion 14 in general to produce nerve stimulation by electrical impulse. Alternatively, nerve stimulation could be carried out by mechanical movement as is also described herein. Still further, mechanical movement could be employed in combination with electrical pulses. These and further means for producing active stimulation should be considered within the scope of the present invention except as it might be expressly limited by the claims. In each instance, the active stimulation portion 14 can have an inactive state where stimulation is not provided and an active state where stimulation is provided.

In the depicted embodiments of FIGS. 1 through 10, the means for producing nerve stimulation comprises a means for producing active nerve stimulation through mechanical movement relative to each of the stimulation surfaces 34 to produce active nerve stimulation through acupressure on the tips of each of the gripping fingers 102, 104, and 106. Mechanical movement and mechanical movement to produce stimulation through acupressure could be accomplished in nearly innumerable ways within the scope of the invention.

In the present embodiment, as best seen perhaps in FIGS. 3 through 6, stimulation of the tips of the user's fingers 102, 104, and 106 is achieved by mechanical movement mechanisms associated with each of the three stimulation surfaces 34. The mechanical movement mechanisms in this embodiment produce periodic projections from the three stimulation surfaces 34.

To produce such periodic projections in the present example, each mechanical movement mechanism has a nodule 36 that is retained for extension and refraction, rotation, or other cyclic or other movement to produce periodic projections from the three stimulation surfaces 34. Here, the nodules 36 comprise cam nodules 36, and each cam nodule 36 is retained by a support axle 38. Each cam nodule 36 can be round or irregularly shaped. Alternatively or additionally, the nodules 36 can have off-center axes of rotation to produce cyclic movement when rotated. The nodules 36 can be formed from any suitable material, such as metal, plastic, rubber, or some other material or combination of materials. The nodules 36 can be rigid, semi-rigid, or resilient. The cam nodules 36 could, for example, take the form of any wheel or disk with a radially extending protrusion, or any wheel that rotates about an axis other than its radial center, or any rotating element that is not circular, such as an ellipse The support axles 38, and thus the nodules 36, are moved, such as to rotate, slide, extend, retract, or undergo some other movement or combination of movements, by a motor 44 with appropriate gearing if necessary. Within the scope of the invention, nodules 36 could be caused only to extend and retract or to oscillate thereby to cause the nodules 36 to be periodically pushed upwardly or outwardly, potentially at an angle. Such movement could advantageously minimize or entirely prevent performance issues, such as malfunctions deriving from a user's grip stopping operation of the motor 44.

In any event, the motor 44 is powered by one or more batteries 30 or another source of power that is in powered association with the motor 44, such as through wiring. Within the scope of the invention, the batteries 30 could be recharged, such as by use of a battery charging port 64 as shown in FIGS. 7 and 8, by wireless recharging, or by any other means for recharging the battery or batteries 30. Other sources of power for the writing utensil 10 are possible, including, for example, manual winding of a coiled spring (not shown) or some other manual energy input. In any event, operation of the motor 44 and thus the active nerve stimulation provided by the nodules 36 can be controlled by a control means 46, such as a switch 46, and electronic circuitry as shown in FIG. 5.

The cam nodules 36 or other means for producing nerve stimulation can be actuated in a pattern, such as by being actuated in series, simultaneously, or in some other pattern. In one contemplated embodiment employing mechanical movement, for instance, the cam nodules 36 can undergo one revolution every approximately three seconds, which is believed to be preferable to avoid what is referred to as nerve accommodation. With this, where one nodule 36 is disposed relative to each of three stimulation surfaces 34, each of the three nodules 36 will be produce nerve stimulation relative to its stimulation surface 34 once over each three-second period.

The stimulation provided to the tips of the fingers 102, 104, and 106 can be selectively or automatically modulated. For example, the cam nodules 36 have a non-round profile such that the stimulation provided to the tips of the fingers 102, 104, and 106 varies during a given rotation of the cam nodules 36. Alternatively or additionally, the speed and possibly the direction of rotation or other movement of the cam nodules 36 can be automatically or selectively modulated, such as by a switch or dial 46, by electronic circuitry, or by gearing. The cam nodules 36 or other active nerve stimulation means can operate simultaneously, consecutively, alternately, or in some other pattern or combination of patterns.

Figure 6:
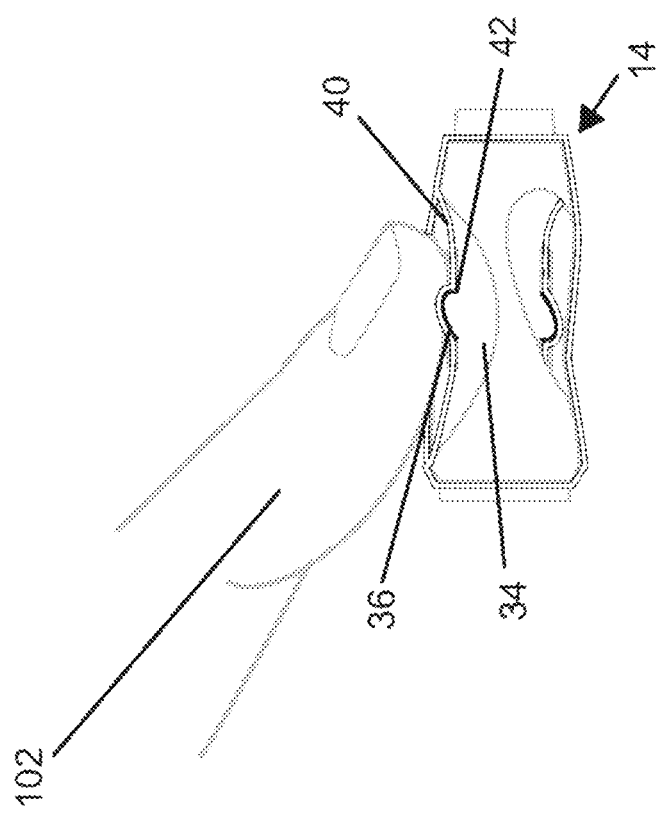
FIG. 6 is a partially sectioned view in side elevation of the active nerve stimulation portion of the writing utensil with a human finger applied for active nerve stimulation.

With particular reference to FIG. 6, one can see that the cam nodules 36 can project through corresponding apertures 42 centrally located in the stimulation surfaces 34. The cam nodules 36 will preferably be disposed with each nodule 36 having a maximum projection through the respective aperture 42 sufficient to produce perceptible nerve stimulation, such as with a light brushing, but not so much as to permit rotation of the cam nodules 36 to be stopped by typical finger pressure. The cam nodules 36 can potentially be resiliently compressible or retained with some resiliency to further prevent unintentional ceasing of the system by a user.

Potentially, a single resilient and flexible sheet 40 or a flexible sheet 40 for each stimulation surface 34 can overly the cam nodules 36 and, potentially, most or all of each of the stimulation surfaces 34. With that, the stimulating movement and pressure of the cam nodules 36 on the tips of the fingers 102, 104, and 106 is exacted through the flexible sheets 40. With this, the pointer finger 102, the middle finger 104, the thumb 106, and any other finger applied to a stimulation surface 34 can be actively stimulated by the writing utensil 10 with active nerve stimulation.

The cam nodules 36 can rotate about lateral but radially spaced axes in relation to the longitudinal axis of the overall writing utensil 10. The rotational or other movement directions of the cam nodules 36 can be the same or different. For example, the cam nodule 36 designed for engaging the pointer finger 102 can rotate toward the distal tip 16 of the writing utensil 10 such that the pointer finger 102 will experience nerve stimulation directed toward the distal end of the finger 102. The cam nodules 36 designed to engage the middle finger 104 and the thumb 106 can rotate toward the proximal end of the writing utensil 10 such that the middle finger 104 and the thumb 106 will experience nerve stimulation directed proximally. Again, one skilled in the art will find obvious other electromechanical devices capable of creating these or similar movements, and each such mechanism is within the scope of the invention except as it might expressly be limited. Embodiments can be universal for left and right handed users or particularized based on hand dexterity.

Under such constructions, when the active stimulation portion 14 is in an active state, a person holding the writing utensil 10 correctly will have acupressure stimulation applied to the tips of the fingers 102, 104, and 106 by the movement of the nodules 36 or other active nerve stimulation. The active stimulation may be unnoticed or marginally noticed by the user, but he or she will feel instant focus and improved energy flow under the theory of operation of the writing utensil 10. This enhanced and precise stimulation will not only tend to train the brain but it will also encourage the correct flow of energy in the hand and body. This encouraged flow will prevent muscular armoring and train the brain and body.

An alternative embodiment of the writing utensil with active nerve stimulation 10 is depicted in FIGS. 7 through 10. There, the writing utensil 10 again has a body portion formed by a central tubular body member 12, a proximal tubular body member 20, and a distally disposed active nerve stimulation portion 14 that has an active state where nerve stimulation is exhibited and an inactive state where it is not. The central tubular body member 12 is coupled to the proximal tubular body member 20 with an O-ring 28 interposed therebetween, and the central tubular body member 12 is coupled to the active nerve stimulation portion 14 with an O-ring 26 interposed therebetween.

A replaceable eraser 22 is retained at the proximal end of the tubular body member 20 with a pocket clip 24 retained by having a ring portion thereof interposed between the replaceable eraser 22 and the tubular body member 20. A conical tip portion 16, which could be magnetized to provide further physiological benefit and impact, is retained at the distal end of the active nerve stimulating portion 14 by a mutual threaded engagement between a coupling member 32 and the nerve stimulating portion 14 to the proximal end thereof and the tip portion 16 to the distal end thereof. Finally, a marking tip, such as a pencil lead 18, can be retained to extend and retract relative to the tip portion 16 and the writing utensil 10 in general.

The active stimulation portion 14 is again disposed to be engaged by the tips of the user's pointer finger 102, middle finger 104, and thumb 106 in a proper utensil grip. The active stimulation portion 14 has first, second, and third evenly spaced stimulation surfaces 34, each presenting an ergonomic surface with a concave or anticlastic curvature for affirmatively receiving and engaging the user's fingers 102, 104, and 106.

As seen in FIGS. 9 and 10, the means for producing nerve stimulation again comprises a means for producing active nerve stimulation through mechanical movement relative to each of the stimulation surfaces 34 to produce active nerve stimulation through acupressure on the tips of each of the gripping fingers 102, 104, and 106. Stimulation of the tips of the user's fingers 102, 104, and 106 is achieved by a mechanical movement mechanism that travels across each of the three stimulation surfaces 34. More particularly, there is a stimulation member 50 that is retained to rotate with an inner sleeve 52 that is itself rotated by a motor 44 through a gearing arrangement 48. The stimulation member 50, which comprises a base pad with at least one protuberance thereon, is rotatably coupled to the inner sleeve 52 to pivot about an axle 58 that is retained by the inner sleeve 52 with an axis that is substantially perpendicular to a tangent of the inner sleeve 52. A guide sleeve 54 slidably receives the inner sleeve 52, and guide channels 56 of varying paths are disposed to encircle the guide sleeve 54. The stimulation member 50 has first and second followers 60 that are received into the guide channels 56. A flexible sheet (not shown) could again overlie the stimulation portion 14.

Under this arrangement, rotation of the inner sleeve 52 will cause the stimulation member 50 to travel circumferentially in relation to the guide sleeve 54 and the writing utensil 10 in general. The travel of the followers 60 along the guide channels 56 will cause the stimulation member 50 to pivot as it travels around the guide sleeve. With this, active nerve stimulation can be provided to the tips of the user's fingers 102, 105, and 106 when the active stimulation portion 14 is in an active state.

An alternative embodiment of the writing utensil with active nerve stimulation 10 is depicted in FIGS. 11 and 12. There, the writing utensil 10 again has a body portion formed by a central tubular body member 12, a proximal tubular body member 20, and a distally disposed active nerve stimulation portion 14. The central tubular body member 12 is coupled to the proximal tubular body member 20, and the central tubular body member 12 is coupled to the active nerve stimulation portion 14.

A replaceable eraser 22 is retained at the proximal end of the tubular body member 20 with a pocket clip 24 retained by having a ring portion thereof interposed between the replaceable eraser 22 and the tubular body member 20. A conical tip portion 16, which could be magnetized to provide further physiological benefit and impact, is retained at the distal end of the active nerve stimulating portion 14 by a mutual threaded engagement between a coupling member 32 and the nerve stimulating portion 14 to the proximal end thereof and the tip portion 16 to the distal end thereof. Finally, a writing tip 18, in this case an ink-pen tip 18, can be retained relative to the tip portion 16 and the writing utensil 10 in general.

The active stimulation portion 14 is again disposed to be engaged by the tips of the user's pointer finger, middle finger, and thumb (not shown in FIGS. 11 and 12) in a proper writing utensil grip. The active stimulation portion 14 has first, second, and third evenly spaced stimulation surfaces 34, each presenting an ergonomic surface with a concave or anticlastic curvature for affirmatively receiving and engaging the user's fingers.

In the present embodiment, however, the active stimulation portion 14, which again has an active state where nerve stimulation is provided and an inactive state where it is not, has an electrical pulse mechanism for providing an electrical pulse to a finger disposed in contact therewith. As a result, nerve stimulation can be provided by electrical impulse when the active stimulation portion 14 is in an active state. While electrical impulse could be exhibited by the stimulation portion 14 in general, the present embodiment has each of the stimulation surfaces 34 provided with an electrical pulse mechanism to provide an electrical pulse to a finger disposed in contact therewith. With that, nerve stimulation can be provided by individual, sequential, or simultaneous electrical impulse relative to the stimulation surfaces 34. The electrical pulses could comprise, for example, high voltage but safe electrical pulses, emitted from each of the stimulation surfaces 34 or the stimulation portion 14 in general to produce nerve stimulation by electrical impulse. The writing utensil with active nerve stimulation 10 of FIGS. 11 and 12 thus comprises a self-contained electric nerve stimulation arrangement.

Figure 13:
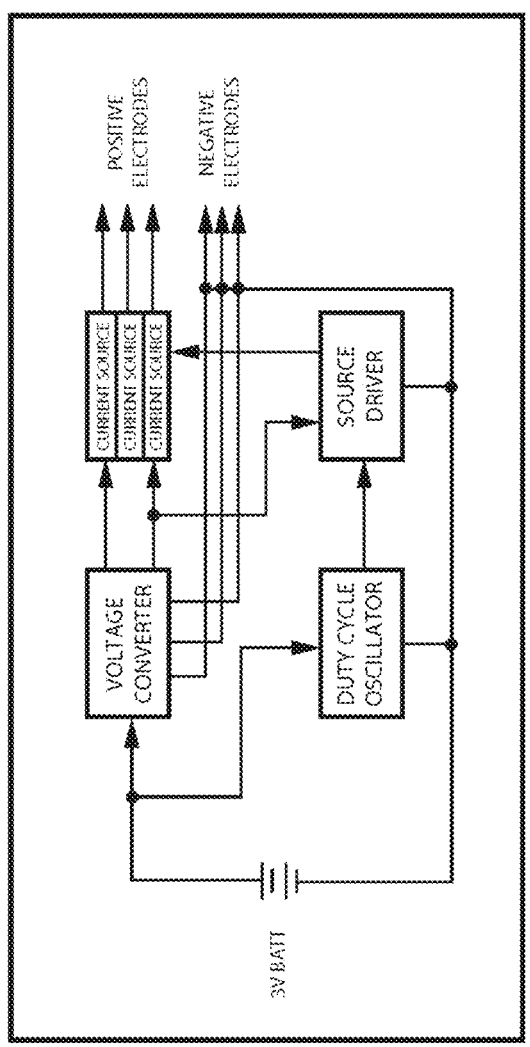
FIG. 13 is an electrical schematic for the writing utensil with active nerve stimulation of FIGS. 11 and 12.

The electronics of the writing utensil 10 can be schematically carried out as shown, for example, in FIG. 13. Of course, after reading this disclosure, one skilled in the art may find a number of alternative electronic configurations for electrically stimulating the tips of the fingers to be possible, and all such configurations are within the scope of the invention except as it might be expressly limited.

In this exemplary embodiment, for each stimulation surface 34, the writing utensil 10 has first and second spaced negative and positive electrodes 60 and 62 for passing electricity from the writing utensil 10 to the respective finger of the user thereby to stimulate the median nerve in the tips of the fingers. The electrodes 60 and 62 can be spaced on each stimulation surface 34 close enough to permit simultaneous contact with a given finger while preventing unintentional electrical interaction. When actuated, current flows from the negative electrode 60 to the positive electrode 62. In one example of the invention, the electrodes 60 and 62 are spaced approximately 3/16 inches apart.

With additional reference to FIG. 13, under certain practices of the invention, the writing utensil 10 can be programmed or otherwise configured such that current flows imparted to the user's thumb and middle finger are different from the current flow imparted to the pointer finger. The electrical impulses can have an electrical repetition rate of approximately 70 pulses per second and a pulse width of 80 microseconds. The battery, which can be a three-volt battery, can be rechargeable in any effective manner, including wirelessly, such as through a wireless charging mat, or by wire to a source of current, such as through an electrical jack or housing. The source of current could, by way of example, comprise an electrical jack or housing for receiving low voltage current from an electrical plug wired to an external transformer (not shown) for receiving electrical power from a source of AC current. As shown in FIG. 13, power from the battery can be circuited to drive a high-voltage converter and a duty cycle oscillator. The major power directing and operational electronics for the invention are also illustrated in FIG. 13.

With continued reference to FIG. 13, the high voltage converter can take the form of a high-frequency oscillator, such as an oscillator of approximately 100 kilohertz, driving a step-up voltage transformer. The step-up transformer can provide a 40-volt pulsed voltage source that can be rectified and filtered to provide a 40-volt DC supply. As contemplated, the duty cycle oscillator is an astable oscillator having preset programming to render an off-time of 14.4 milliseconds and an on-time of 80 microseconds, which can be sent simultaneously, in series, or in some pattern to each stimulating surface 34. The duty cycle oscillator drives a current source driver that converts a low voltage output signal for the duty cycle oscillator into a high voltage signal to drive three high-voltage current sources. The current sources are configured to provide a variable amplitude current pulse into a 500-ohm AAMI or resistive load. As contemplated, the substantial part of the discharge of the batteries occurs at 2.4 volts giving a maximum current pulse amplitude of about 50 milliamperes.

As shown in FIG. 13, there can be a normally open output circuit between each positive electrode and each negative electrode. The normally open output circuits receive the high voltage output of the operational electronics held in the housing of the writing utensil 10. Variable current pulse amplitude control is provided by a variable resistor in the current flow through the normally open output circuit when closed.

As shown in FIG. 11, located on the body member 20 of the utensil 10 is a control mechanism 46, such as a control knob 46. The control knob 46 serves as an on/off switch to control current flow between the battery or batteries and the operational electronics held in the body members 12, 24, and 20. As such, the control knob 46 allows manual setting of operational characteristics of the writing utensil 10, including manipulation between an active state where active nerve stimulation by electrical impulse is exhibited and an inactive state where active nerve stimulation is not exhibited. The control knob 46 can additionally be enabled to adjust, among other things, the current pulse amplitude. Though the circuitry is capable of providing 0-70 milliamperes at full battery charge, current limiting is provided to keep the maximum current pulse amplitude at a 50-milliampere level consistent with normal battery operating conditions.

With certain details of the present invention for a writing utensil 10 disclosed, it will be appreciated by one skilled in the art that changes and additions could be made thereto without deviating from the spirit or scope of the invention. This is particularly true when one bears in mind that the presently preferred embodiments merely exemplify the broader invention revealed herein. Accordingly, it will be clear that those with certain major features of the invention in mind could craft embodiments that incorporate those major features while not incorporating all of the features included in the preferred embodiments.

Therefore, the following claims are intended to define the scope of protection to be afforded to the inventor. Those claims shall be deemed to include equivalent constructions insofar as they do not depart from the spirit and scope of the invention. It must be further noted that a plurality of the following claims may express certain elements as means for performing a specific function, at times without the recital of structure or material. As the law demands, these claims shall be construed to cover not only the corresponding structure and material expressly described in this specification but also all equivalents thereof that might be now known or hereafter discovered.

I claim as deserving the protection of Letters Patent:

1. A writing utensil with active nerve stimulation for providing active nerve stimulation to the fingertips of a user, the writing utensil comprising:
   a body portion with a proximal end and a distal end;
   a tip portion coupled to the distal end of the body portion wherein the tip portion has means for retaining a marking tip; and
   an active stimulator with at least one active stimulation surface disposed adjacent to the distal end of the body portion to be engaged by the fingertips of the user wherein the active stimulator has an active state wherein active nerve stimulation is provided to fingertips of the user in contact with the active stimulation surface and an inactive state wherein active stimulation is not provided to fingertips of the user in contact with the active stimulation surface, wherein the active stimulator has at least one mechanical movement mechanism with an active state wherein cyclical mechanical movement is exhibited in relation to the active stimulation surface and an inactive state, and wherein the mechanical movement mechanism produces a periodic extension relative to the active stimulation surface when the active stimulator is in an active state;
   wherein the active stimulator has first, second, and third different active stimulation surfaces, each stimulation surface for engaging a fingertip of the user, wherein the first, second, and third active stimulation surfaces generally form a triangle in lateral cross section with the first, second, and third active stimulation surfaces spaced around a peripheral surface of the body portion adjacent to the distal end of the body portion, and wherein the mechanical movement mechanism produces a periodic extension relative to each of the first, second, and third active stimulation surfaces when the active stimulator is in an active state.

2. The writing utensil with active nerve stimulation of claim 1 wherein each active stimulation surface has a concave curvature for receiving and engaging a fingertips of the user.

3. The writing utensil with active nerve stimulation of claim 1 wherein each active stimulation surface has an anticlastic curvature for receiving and engaging a fingertip of the user.

4. The writing utensil with active nerve stimulation of claim 1 wherein the mechanical movement mechanism comprises at least one nodule and means for cyclically causing at least a portion of the nodule to extend periodically relative to the active stimulation surface.

5. The writing utensil with active nerve stimulation of claim 4 wherein the nodule comprises a cam nodule with an eccentric portion and wherein the means for cyclically causing at least a portion of the nodule to extend periodically relative to the active stimulation surface comprises a means for rotating the cam nodule.

6. The writing utensil with active nerve stimulation of claim 1 wherein the active stimulator further comprises a motor and a power source for the motor.

7. The writing utensil with active nerve stimulation of claim 1 wherein the active stimulator actuates the mechanical movement mechanism to produce periodic extensions in relation to the first, second, and third active stimulation surfaces in a sequential pattern.

8. The writing utensil with active nerve stimulation of claim 7 wherein a cam nodule with an eccentric portion is disposed to cause the eccentric portion of the cam nodule to extend periodically relative to each of the first, second, and third active stimulation surfaces and wherein the means for cyclically causing at least a portion of the cam nodule to extend periodically relative to the active stimulation surface comprises a means for rotating the cam nodule.

9. The writing utensil with active nerve stimulation of claim 8 further comprising a resilient sheet overlying the can nodule for being interposed between the fingertip of the user and the cam nodule.

10. The writing utensil with active nerve stimulation of claim 1 further comprising a control mechanism for actuating the active stimulator between active and inactive states.

11. The writing utensil of claim 1 wherein the mechanical movement mechanism comprises a motor, a power source for the motor, an inner sleeve, a stimulation member with at least one follower wherein the stimulation member is retained exterior to the inner sleeve to move with the inner sleeve, a guide sleeve concentrically disposed to receive the inner sleeve, and guide channels in the guide sleeve for receiving the follower of the stimulation member wherein rotation of the inner sleeve causes the stimulation member to travel circumferentially in relation to the guide sleeve and the writing utensil and with the at least one follower to travel along the channels in the guide sleeve to produce a periodic extension relative to each of the first, second, and third active stimulation surfaces when the active stimulator is in an active state.

12. A writing utensil with active nerve stimulation for providing active nerve stimulation to the fingertips of a user, the writing utensil comprising:
a body portion with a proximal end and a distal end;
a tip portion coupled to the distal end of the body portion wherein the tip portion has means for retaining a marking tip; and
an active stimulator with at least one active stimulation surface disposed adjacent to the distal end of the body portion to be engaged by the fingertips of the user wherein the active stimulator has an active state wherein active nerve stimulation is provided to fingertips of the user in contact with the active stimulation surface and an inactive state wherein active stimulation is not provided to fingertips of the user in contact with the active stimulation surface, wherein the active stimulator has at least one mechanical movement mechanism with an active state wherein cyclical mechanical movement is exhibited in relation to the active stimulation surface and an inactive state, and wherein the mechanical movement mechanism produces a periodic extension relative to the active stimulation surface when the active stimulator is in an active state;
wherein the mechanical movement mechanism comprises a motor, a power source for the motor, an inner sleeve, a stimulation member with at least one follower wherein the stimulation member is retained exterior to the inner sleeve to move with the inner sleeve, a guide sleeve concentrically disposed to receive the inner sleeve, and guide channels in the guide sleeve for receiving the follower of the stimulation member wherein rotation of the inner sleeve causes the stimulation member to travel circumferentially in relation to the guide sleeve and the writing utensil and with the at least one follower to travel along the channels in the guide sleeve.

* * * * *